US011806928B2

United States Patent
Cropper et al.

(10) Patent No.: US 11,806,928 B2
(45) Date of Patent: Nov. 7, 2023

(54) ADDITIVE MANUFACTURING WITH A PLURALITY OF MATERIALS

(71) Applicant: 3D PROMED, LLC, Mesa, AZ (US)

(72) Inventors: Dean E. Cropper, Ashland, OR (US); Joseph T. Zachariasen, Medform, OR (US)

(73) Assignee: 3D Promed, LLC, Mesa, AZ (US)

( * ) Notice: Subject to any disclaimer, the term of this patent is extended or adjusted under 35 U.S.C. 154(b) by 0 days.

(21) Appl. No.: 16/481,432

(22) PCT Filed: Jan. 26, 2018

(86) PCT No.: PCT/US2018/015569
§ 371 (c)(1),
(2) Date: Jul. 26, 2019

(87) PCT Pub. No.: WO2018/151923
PCT Pub. Date: Aug. 23, 2018

(65) Prior Publication Data
US 2019/0344494 A1    Nov. 14, 2019

Related U.S. Application Data

(60) Provisional application No. 62/451,037, filed on Jan. 26, 2017.

(51) Int. Cl.
*B29C 64/112* (2017.01)
*B29C 64/209* (2017.01)
(Continued)

(52) U.S. Cl.
CPC .......... *B29C 64/209* (2017.08); *A61K 9/7007* (2013.01); *B22F 10/22* (2021.01);
(Continued)

(58) Field of Classification Search
CPC ... B22F 2207/01; B29C 64/112; B29C 64/209
See application file for complete search history.

(56) References Cited

U.S. PATENT DOCUMENTS 8,029,096 B2    10/2011  Silverbrook
2006/0105011 A1*  5/2006  Sun .................. G06F 30/00
                                                 424/422

(Continued)

OTHER PUBLICATIONS

USPTO as International Searching Authority, "International Search Report and Written Opinion," International Application No. PCT/US2018/015569, dated May 14, 2018.

*Primary Examiner* — James Sanders
(74) *Attorney, Agent, or Firm* — DENTONS Durham Jones Pinegar

(57) ABSTRACT

A method for fabricating an article of manufacture includes forming a plurality of layers of the article based on a digital model of the article. Each layer of the plurality of layers may be formed by depositing at least two materials that differ from one another. The at least two materials may be deposited separately or simultaneously. The at least two materials may define separate regions of the layer and, thus, define distinct features of the article, and/or the at least two materials may be mixed or one of the materials may be dispersed throughout the other to define a blended zone in the layer. Blended zones of adjacent layers may be superimposed to define three-dimensional blended zones. A blended zone may be graded to provide transition between separate regions of the article that are formed from two or more different materials. Articles fabricated by such processes are also disclosed.

19 Claims, 2 Drawing Sheets

(51) Int. Cl.
*B33Y 10/00* (2015.01)
*B33Y 80/00* (2015.01)
*B32B 7/025* (2019.01)
*B32B 7/027* (2019.01)
*A61K 9/70* (2006.01)
*B33Y 70/10* (2020.01)
*B22F 10/22* (2021.01)
*B22F 12/55* (2021.01)

(52) U.S. Cl.
CPC ............ *B29C 64/112* (2017.08); *B32B 7/025* (2019.01); *B32B 7/027* (2019.01); *B33Y 10/00* (2014.12); *B33Y 70/10* (2020.01); *B33Y 80/00* (2014.12); *B22F 12/55* (2021.01); *B29K 2995/0005* (2013.01); *B29K 2995/0013* (2013.01)

(56) References Cited

U.S. PATENT DOCUMENTS

| | | | |
|---|---|---|---|
| 2015/0044084 A1* | 2/2015 | Hofmann | B05D 1/18 264/642 |
| 2015/0360427 A1 | 12/2015 | Shah et al. | |
| 2016/0136887 A1 | 5/2016 | Guillemette et al. | |
| 2016/0185009 A1 | 6/2016 | Keshavan et al. | |
| 2017/0326785 A1 | 11/2017 | MacCurdy et al. | |
| 2018/0264719 A1* | 9/2018 | Rolland | G03F 7/029 |

* cited by examiner

ADDITIVE MANUFACTURING WITH A PLURALITY OF MATERIALS

CROSS-REFERENCE TO RELATED APPLICATION

Claims for priority are hereby made to the Jan. 26, 2018 filing date of PCT Application No. PCT/US2018/015569, titled ADDITIVE MANUFACTURING WITH A PLURALITY OF MATERIALS ("the '569 PCT Application") and to the Jan. 26, 2017 filing date of U.S. Provisional Patent Application No. 62/451,037, titled ADDITIVE MANUFACTURING WITH A PLURALITY OF MATERIALS ("the '037 Provisional Application"). For purposes of the United States, the application is also a continuation-in-part of U.S. patent application Ser. No. 15/297,092, filed on Oct. 18, 2016 and titled USE OF ADDITIVE MANUFACTURING PROCESSES IN THE MANUFACTURE OF CUSTOM WEARABLE AND/OR IMPLANTABLE MEDICAL DEVICES ("the '092 Application"), now U.S. Pat. No. 10,675,855, issued on Jun. 9, 2020, which is a continuation of U.S. patent application Ser. No. 14/808,203, filed on Jul. 24, 2015 and titled USE OF ADDITIVE MANUFACTURING PROCESSES IN THE MANUFACTURE OF CUSTOM WEARABLE AND/OR IMPLANTABLE MEDICAL DEVICES ("the '203 Application"), now U.S. Pat. No. 9,469,075, issued on Oct. 18, 2016, which is a continuation in part of U.S. patent application Ser. No. 14/139,489, filed on Dec. 23, 2013 and titled USE OF ADDITIVE MANUFACTURING PROCESSES IN THE MANUFACTURE OF CUSTOM ORTHOSES ("the '489 Application"), now U.S. Pat. No. 9,610,731, issued Apr. 4, 2017. The '489 Application included claims for priority under 35 U.S.C. § 119(e) to the Dec. 22, 2012 filing date of U.S. Provisional Patent Application No. 61/745,557, titled USE OF ADDITIVE MANUFACTURING PROCESSES IN THE MANUFACTURE OF CUSTOM ORTHOSES, ("the '557 Provisional Application") and to the Mar. 15, 2013 filing date of U.S. Provisional Patent Application No. 61/800,582, also titled USE OF ADDITIVE MANUFACTURING PROCESSES IN THE MANUFACTURE OF CUSTOM ORTHOSES, ("the '582 Provisional Application"). The entire disclosures of the '569 PCT Application, the '037 Provisional Application, the '092 Application, the '203 Application, the '489 Application, the '557 Provisional Application, and the '582 Provisional Application are hereby incorporated herein.

TECHNICAL FIELD

This disclosure relates to methods for fabricating articles of manufacture. More specifically, this disclosure relates to additive manufacturing methods in which two or more materials with different physical properties are deposited in the same layer. The two or more materials may be deposited separately or simultaneously. The two or more materials may be deposited in such a way that the materials can be blended within a layer of an article manufactured by such an additive manufacturing method. Blended zones may provide transitions between the two or more materials, from which such blended zones are formed, and may extend laterally (i.e., in two dimensions) in a single layer or a sequence of adjacent layers, comprise transition zones that extend transversely through a sequence of adjacent layers, and/or they may extend in three dimensions, with transitions occurring both laterally within one or more layers and transversely between two or more adjacent layers. This disclosure also relates to articles that may be made by the disclosed additive manufacturing methods.

RELATED ART

Articles of manufacture that include features formed from different materials have historically been built by manufacturing each discrete feature from its respective material and securing adjacent features to one another. For many articles, separate features are independently fabricated or manufactured and then assembled and, if necessary, secured to each other (e.g., with adhesive materials, by welding or brazing, with mechanical fasteners, etc.). Other articles may be manufactured by making a first feature, then making a second feature on the first feature (e.g., semiconductor fabrication processes, etc.). For still other articles, separate features may be made simultaneously, and they may be secured together as they are made (e.g., in co-molding processes, etc.).

The availability and popularity of additive manufacturing processes have increased steadily in recent years. Existing additive manufacturing processes have been used to make models or prototypes from a single material. Limitations on the types of materials that have conventionally been useful in additive manufacturing processes have largely restricted the use of such processes to manufacturing models or prototypes from materials that may not have properties needed to enable the models or prototypes to function in the same manner intended for the corresponding finished article.

DISCLOSURE

An article of manufacture according to this disclosure includes a plurality of layers that are adjacent to one another and at least partially superimposed with respect to each other. Each layer of the plurality of layers may be defined by a plurality of adjacent, integrated sections configured to impart the article of manufacture with at least two different properties. The plurality of adjacent, integrated sections of each layer may include a first section defined by a first material with a first physical property and a second section defined by a second material with a second physical property.

In some embodiments, a discrete boundary may be defined between adjacent sections of a layer of an article of manufacture. The different sections of such an embodiment may provide different functions from each other. For example, one section of a layer may be electrically conductive to enable a feature of which it is a part (e.g., a layer of, if the part is formed from at least partially superimposed sections a plurality of adjacent layers, etc.) to convey electricity (e.g., to supply power, as a signal to convey data, etc.). Another section of the layer may be electrically insulative to enable a feature of which it is a part (e.g., a layer of, if the part is formed from at least partially superimposed sections a plurality of adjacent layers, etc.). The electrically insulative section of the layer, and the feature of which it is a part, may electrically insulate at least a portion of an adjacent electrically conductive section. In a similar combination, a thermally conductive material may be used to define one section of a layer, while a thermally insulative material may be used to define another feature of the layer.

In another example, one section of a layer may be formed from a flexible material while another section may be formed from a material (or a combination of materials) that may selectively change one or more of its phase, crystalline structure, size, and shape. The section formed from such a material (or materials) may define part of a feature that may be selectively structurally manipulated (e.g., its shape, size, crystalline structure, phase, etc.) (e.g., to enable movement of the article of manufacture or a portion thereof, etc.). The section formed from flexible material may be capable of flexing or absorbing movement by the structurally manipulatable feature.

As still another example, a collection of sections of a layer (which may or may not include contiguous sections) may form part of a matrix, while another collection of sections of the layer (which may or may not include contiguous sections) may be defined by a material supported by the matrix or dispersed throughout the matrix.

In other embodiments, blended zones may be defined between sections of a layer that are formed from different materials. A blended zone may comprise a transition between sections of a layer that are separately defined by the two materials that form the blended zone. For example, a first section of the layer may include, consist essentially of, or consist of a first material, a second section of the layer may include, consist essentially of, or consist of a second material, and a blended zone between the first and second sections may include a graded area that provides a transition from the first material to the second material.

In various embodiments, a blended zone may include two or more materials that have combined (e.g., to form a mixture, to form a compound, etc.), it may include two materials that are interdispersed, it may include a first material throughout which one or more additional materials are dispersed, or it may include any combination of the foregoing.

In some articles of manufacture, a blended zone may only extend laterally through one layer or through at least partially superimposed portions of a series of adjacent layers. In other articles of manufacture, a blended zone may extend through a series of adjacent layers, in a direction transverse to the planes of the series of adjacent layers. Other articles of manufacture may include blended zones that extend both laterally across at least partially superimposed portions a series of adjacent layers and transversely through the series of adjacent layers.

Similarly, the grading and/or other blending of a blended zone in an article of manufacture may only extend laterally through one layer or through at least partially superimposed portions of a series of adjacent layers. In some articles of manufacture, a transition zone may extend through a series of adjacent layers, in a direction transverse to the planes of the series of adjacent layers (i.e., vertically). Other articles of manufacture may include both blended zones that extend laterally across at least partially superimposed portions of a series of adjacent layers and transition zones that extend transversely between adjacent layers or through a series of three or more adjacent layers.

A transition zone may impart the article of manufacture of which the layer is a part with a desired property. In some embodiments, that property may be a particular function. In other embodiments, a transition zone may promote adhesion between two or more different materials that define adjacent sections of a layer between sections of a series of adjacent different layers that are formed from two or more different materials and that are at least partially superimposed relative to one another. Other embodiments of articles of manufacture according to this disclosure may include blended zones and/or transition zones that enable materials that may otherwise be somewhat incompatible to be used in proximity or next to each other.

Various combinations of materials that may be used to fabricate an article of manufacture according to this disclosure include, but are not limited to, rigid materials and flexible materials (e.g., materials with different hardnesses, or durometers, etc.); structural materials and cushioning materials (e.g., materials with different hardnesses, or durometers, etc.); different types of polymers and/or polymer-based composite materials; electrically conductive materials and electrically insulative materials (e.g., metals and polymers, conductive polymers, and dielectric polymers, etc.); thermally conductive materials and thermally insulative materials; transparent materials, translucent materials, and/or opaque materials; organic materials and inorganic materials (e.g., polymers or polymer-based composite materials and metal(s), polymers or polymer-based composite materials and glass and/or a ceramic material, etc.); biological materials (e.g., cells, viruses, etc.) and non-biological materials (e.g., nutrients); pharmaceutical materials (e.g., drugs, etc.) and excipient materials; and the like.

An additive manufacturing method according to this disclosure may include forming one or more layers of an article of manufacture by depositing two or more materials that differ from one another. The two or more materials may be deposited in a predetermined sequence (e.g., by programming that runs additive manufacturing equipment, or a "digital model," etc.). In some embodiments, two or more materials may be deposited simultaneously to define at least a portion of a layer of the article of manufacture. Simultaneous deposition may enable simultaneous fabrication of separate parts of a layer, compounding of the materials in a blended zone or a transition zone, dissolution of one of the materials within another of the materials in a blended zone or a transition zone, dispersion of one of the materials throughout another of the materials in a blended zone or a transition zone, any other desired type of blending, or any combination of the foregoing. Once a layer of the article of manufacture has been defined, a subsequent layer of the article of manufacture may be formed over the previously formed layer. The previously formed layer may be allowed to completely cure or solidify before the subsequent layer is formed. Alternatively, the subsequent layer may be formed before the previously formed layer has completely cured or solidified. Depending on the extent to which the previously layer has cured or solidified before the subsequent layer is formed, and possibly depending on the properties of the adjacent and/or blended materials, the adjacent layers may be discrete from one another (i.e., there may be a discernible boundary between them) or they may include a vertically blended region, or transition zone.

The two or more materials may be deposited in a manner that defines adjacent, discrete (e.g., with a discernable boundary therebetween, with a transition zone that may only be seen by an individual with the aid of magnification, etc.) sections of the layer. Likewise, discrete boundaries may exist between regions of at least partially superimposed layers that are also at least partially superimposed with respect to one another and that are defined by different materials.

Alternatively, the two or more materials may be deposited in a manner that defines a blended zone in the layer and/or a transition zone with an adjacent layer. In some embodiments, two or more materials may be deposited in a manner that provides grading across and/or through the blended zone and/or transition zone, resulting in a blended zone between two or more sections of a layer and/or a transition zone between at least partially superimposed regions of two or more sequentially adjacent layers that are at least partially superimposed with respect to one another.

An additive manufacturing method according to this disclosure may be used to manufacture an article of manufacture according to this disclosure. It may also be possible to define an article of manufacture according to this disclosure using other techniques.

In another aspect, this disclosure includes systems for generating digital models of articles of manufacture and, thus, operating instructions (e.g., .stl files or other suitable files) for use by additive manufacturing equipment that will enable such equipment to carry out a method according to this disclosure and/or that will enable the manufacture of an article according to this disclosure. In addition to including a plurality of at least partially superimposed/superimposable digital layers, a digital model according to this disclosure may define the material and/or materials that define different sections of each layer of the article of manufacture that the digital model may be used to fabricate. The digital model may also include the shape and dimensions of each blended zone. Optionally, a digital model according to this disclosure may define the materials that define any blended zones in each layer of the article of manufacture, transition zones between adjacent portions of superimposed layers of the article of manufacture, and/or transition zones through a series of three or more superimposed layers of the article of manufacture that correspond to the digital model, as well as the relative proportions of the materials and any grading from one or more materials to one or more other materials across each blended zone and/or transition zone in the article of manufacture.

Additive manufacturing equipment capable of carrying out the disclosed additive manufacturing methods are also disclosed. Such equipment, which may operate under control of a digital model according to this disclosure, includes reservoirs for a plurality of different materials, as well as one or more print heads. In some embodiments, the additive manufacturing equipment may include an individual print head for each of the plurality of different materials. In other embodiments, two or more materials may be deposited by the same print head, which may also be referred to herein as a "common print head." A common print head may be capable of depositing different materials at distinct intervals of time (e.g., in a programmed sequence, etc.) and/or simultaneously.

Other aspects of this disclosure, as well as features and advantages of the disclosed subject matter, will become apparent to those of ordinary skill in the art through consideration of the foregoing disclosure and the appended claims.

DETAILED DESCRIPTION

Figure 1:
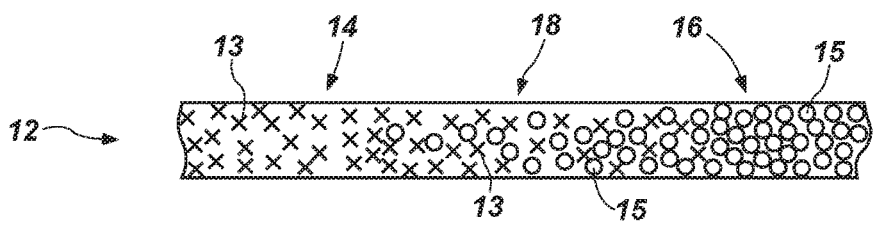
FIG. 1 represents a layer of an article of manufacture that has been formed from different materials, with the layer including a blended zone comprising a transition between sections that consist of or consist essentially of each of the different materials.

With reference to FIG. 1, an embodiment of a layer 12 of an article of manufacture is depicted. The layer 12 is formed from two different materials—a first material 13 and a second material 15. The first material 13 defines a first section 14 of the layer 12. The first section 14 may comprise the first material 13, consist essentially of the first material 13, or consist of the first material 13. The second material 15 defines a second section 16 of the layer 12. The second section 16 may comprise the second material 15, consist essentially of the second material 15, or consist of the second material 15. In addition to the first section 14 and the second section 16, the layer 12 may include one or more blended zones 18. As illustrated by FIG. 1, in the blended zone 18, the first material 13 and the second material 15 are mixed, or blended.

Figure 1A:
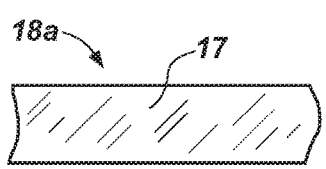
FIG. 1A illustrates a blended zone in which the different materials have dissolved into each other to form a new material.
Figure 1B:
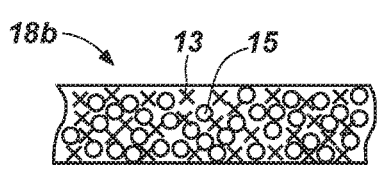
FIG. 1B illustrates a blended zone in which the different materials have interdispersed.
Figure 1C:
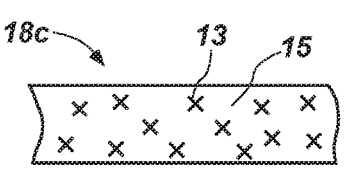
FIG. 1C illustrates a blended zone in which one material has dispersed throughout another material.

The first material 13 and the second material 15 may be mixed, or blended, in any number of ways in the blended zone 18. FIGS. 1A-1C illustrate a few non-limiting embodiments of the manner in which the first material 13 and the second material 15 may be mixed.

In FIG. 1A, the first material 13 (FIG. 1) and the second material 15 (FIG. 1) in a blended zone 18a have blended in such a way that a new material 17 has been formed. Without limitation, one of the first material 13 and the second material 15 may have dissolved in the other or the first material 13 and the second material 15 may be miscible, or the first material 13 and the second material 15 may have reacted with one another.

FIG. 1B illustrates an embodiment of blended zone 18b in which the first material 13 and the second material 15 have interspersed with one another. Stated another way, the first material 13 and the second material 15 are mixed, but have not combined with one another to define a new material.

The blended zone 18c illustrated by FIG. 1C includes a first material 13 that has been dispersed throughout a second material 15.

While FIGS. 1A-1C depict homogeneous mixing of different materials 13 and 15, it should be appreciated by those of ordinary skill in the art that different materials may also be mixed to form gradients, as depicted in the blended zone 18 of the layer 12 shown in FIG. 1.

Figure 2:
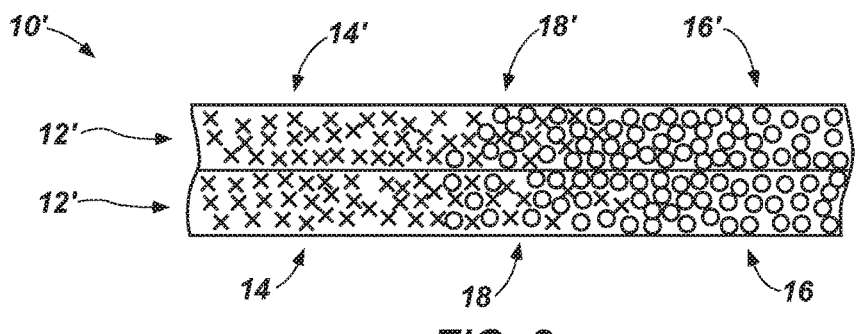
FIG. 2 depicts an article of manufacture including adjacent, superimposed layers that include blended zones, with the blended zones of the adjacent, superimposed layers being at least partially superimposed with one another.

FIG. 2 depicts an embodiment of an article of manufacture 10' in which adjacent, at least partially superimposed layers 12 and 12' include blended zones 18 and 18', respectively, that are also at least partially superimposed. FIG. 2 shows that blended zones 18 and 18' of two or more materials may extend partially or completely through an article of manufacture 10'.

Figure 3:
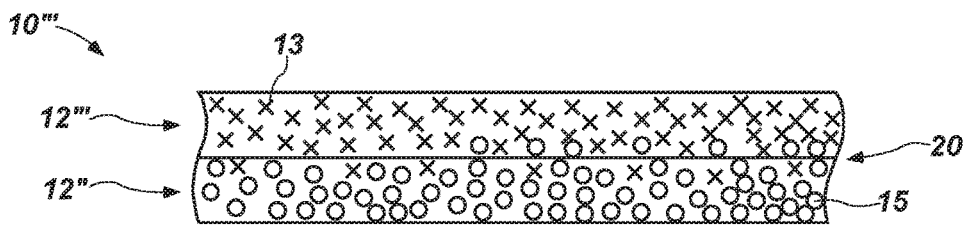
FIG. 3 depicts an article of manufacturing including adjacent, superimposed layers formed from different materials, with blending of the materials at a transition zone between the adjacent, superimposed layers.

As illustrated by FIG. 3, blending may also occur between adjacent layers 12" and 12''' of an article of manufacture 10'. More specifically, FIG. 3 depicts an article of manufacture 10' in which one layer 12' is formed from a first material 13 and another layer 12 is formed from a second material 15. The layers 12" and 12''' may be from materials 13 and 15 that blend upon contacting each other and/or the previously formed layer 12" may not completely cure or harden before forming the subsequent layer 12'''. The result may be a transition zone 20 (as opposed to a discernible boundary) between the adjacent, superimposed layers 12" and 12'''.

Figure 4:
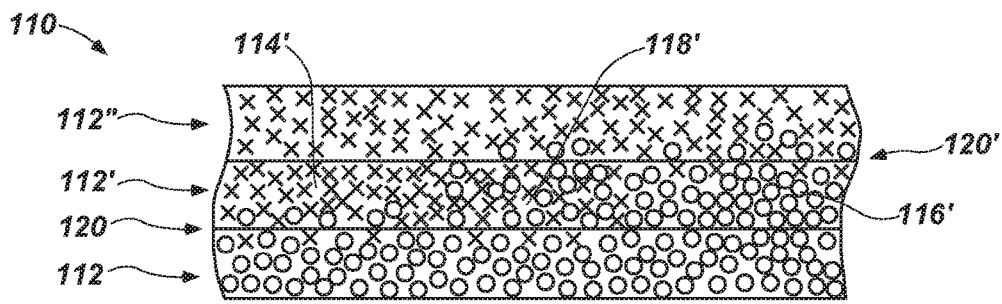
FIG. 4 depicts an article of manufacture in which blending of materials occurs in three-dimensions, including within layers, between layers, and across a series of layers.

FIG. 4 illustrates an embodiment of an article of manufacture 110 that includes both a blended zone 118' in one or more layers 112, 112', 112" (the blended zone 118' appears primarily in layer 112') and a transition zone 120, 120' between adjacent, superimposed layers 112 and 112', 112' and 112" and/or a transition zone across a series of superimposed layers 112, 112', 112". As illustrated by FIG. 4, different materials of an article of manufacture 110 formed by additive manufacturing processes may blend three-dimensionally.

Figure 5:
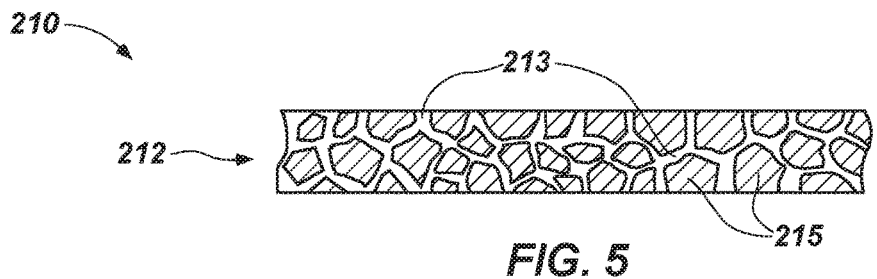
FIG. 5 represents a layer of an article of manufacture that includes a matrix formed from a first material and a second material located within the matrix.

Additive manufacturing processes that include the use of two or more materials may also be used to form an article of manufacture 210 such as that depicted by FIG. 5, which includes a layer 212 that includes a matrix 213 formed from a first material and a second material 215 within the matrix 213.

Figure 6:
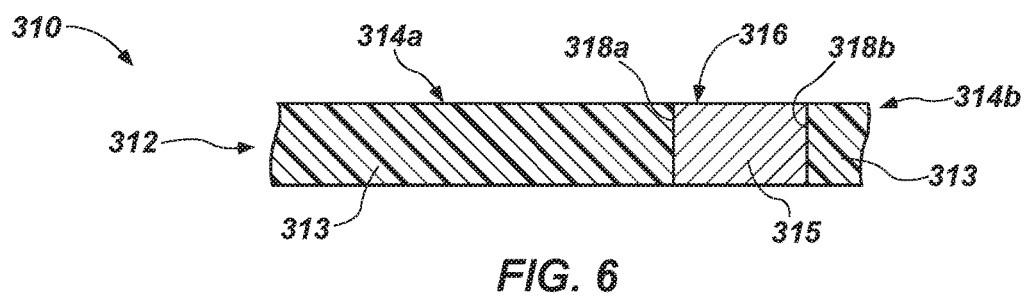
FIG. 6 represents a layer of an article of manufacture with discrete sections formed from different materials.

In addition, additive manufacturing processes may be used to fabricate an article of manufacture 310 such as that depicted by FIG. 6, which includes at least one layer 312 with one or more first sections 314a, 314b formed from a first material 313 and one or more discrete second sections 316 formed from a second material 315. A discernible boundary 318a, 318b may exist between each first section 314a, 314b and each adjacent second section 316. In a specific, but non-limiting embodiment, The first material 313 may comprise an electrically insulative material and the second material 315 may comprise an electrically conductive material. In other embodiments, the first material 313 and the second material 315 could comprise materials with any combination of different physical properties. Some non-limiting examples include materials with different thermal conductivities, electromagnetic transparencies/opacities, rigidities/flexibilities, hardnesses, strengths, and the like.

Figure 7:
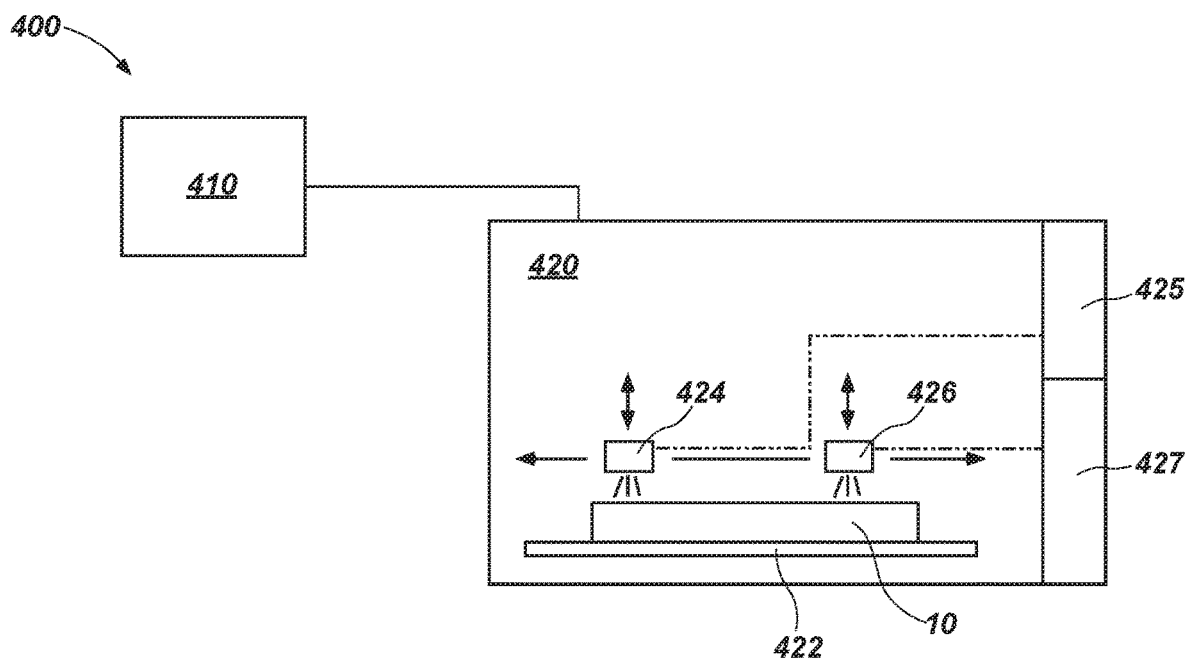
FIG. 7 provides a schematic representation of a system for fabricating an article of manufacture according to this disclosure.

Turning now to FIG. 7, an embodiment of a system 400 for fabricating articles of manufacture is depicted. Such a system 400 may include a processing component 410 and additive manufacturing equipment 420. The processing component 410 may be programmed to generate digital models of articles of manufacture and, thus, operating instructions (e.g., .stl files or other suitable files) for use by the additive manufacturing equipment 420. A digital model may define the structure (in layers, etc.) of an article of manufacture 10, as well as the material and/or materials that define different areas or sections of each layer of the article of manufacture 10 that the digital model may be used to fabricate. The digital model may also include the shape and dimensions of each blended zone and/or transition zone. Optionally, a digital model may define the materials that define any blended zones in each layer of the article of manufacture 10, transition zones between adjacent portions of superimposed layers of the article of manufacture 10, and/or transition zones through a series of three or more superimposed layers of the article of manufacture 10 that correspond to the digital model, as well as the relative proportions of the materials and any grading from one or more materials to one or more other materials across each blended zone and/or transition zone in the article of manufacture.

Upon execution of appropriate operating instructions, the additive manufacturing equipment 420 may fabricate a corresponding article of manufacture 10. The additive manufacturing equipment may include reservoirs 425 and 427 for a plurality of different materials, as well as one or more print heads 424, 426 for dispensing the different materials. In some embodiments, the additive manufacturing equipment 420 may include an individual print head 424, 426 for each of the plurality of different materials. In other embodiments, two or more materials may be deposited by the same print head, which may also be referred to herein as a "common print head." A common print head may be capable of depositing different materials at distinct intervals of time (e.g., in a programmed sequence, etc.) and/or simultaneously.

Although the foregoing disclosure sets forth many specifics, these should not be construed as limiting the scope of any of the claims, but merely as providing illustrations of some embodiments and variations of elements and/or features of the disclosed subject matter. Other embodiments of the disclosed subject matter may be devised which do not depart from the spirit or scope of any of the claims. Features from different embodiments may be employed in combination. Accordingly, the scope of each claim is limited only by its plain language and the legal equivalents thereto.

What is claimed:

1. A method for fabricating an article of manufacture, comprising:

forming a layer of the article of manufacture based on a digital model of the article of manufacture using an additive manufacturing system, the layer formed from at least two materials in liquid form that differ from one another, the at least two materials being miscible, at least one of the at least two materials able to dissolve at least another material of the at least two materials, or the at least two materials able to react with one another; and repeating the forming at least once to form another layer of the article of manufacture, the another layer of the article of manufacture being at least partially superimposed with the layer of the article of manufacture, the at least two materials forming at least one blended zone including at least portions of the layer and the another layer, the at least one blended zone approximating a boundary between the layer and the another layer.

2. The method of claim 1, wherein forming the layer of the article of manufacture comprises depositing the at least two materials simultaneously.

3. The method of claim 1, wherein forming the at least one blended zone comprises dispersing at least one of a first material of the at least two materials and a second material of the at least two materials throughout the other of the first material and the second material.

4. The method of claim 3, wherein forming the at least one blended zone comprises forming a transition zone between a first area of the layer consisting essentially of the first material and a second area of the layer consisting essentially of the second material.

5. The method of claim 4, wherein forming the transition zone comprises grading the first material and the second material from the first area to the second area.

6. The method of claim 1, wherein repeating the forming at least once comprises depositing the at least two materials of the another layer at a location at least partially superimposed with a location at which the at least two materials of the layer were deposited.

7. The method of claim 6, wherein forming the layer and repeating the forming at least once comprise forming a graded area through a plurality of layers.

8. The method of claim 1, wherein forming the layer of the article of manufacture comprises depositing at least two compatible materials simultaneously.

9. The method of claim 1, wherein forming the layer of the article of manufacture comprises providing a transition between the at least two materials to promote adhesion of the layer to the another layer.

10. The method of claim 1, wherein forming the layer of the article of manufacture comprises defining a structure in which a first material of the at least two materials defines a three-dimensional matrix throughout at least a portion of the article of manufacture and a second material of the at least two materials is dispersed throughout and/or supported by the three-dimensional matrix.

11. The method of claim 1, wherein forming the layer of the article of manufacture comprises depositing:
   at least two materials with different electrical conductivities; or
   at least two materials with different thermal conductivities.

12. The method of claim 1, wherein forming the layer of the article of manufacture comprises depositing a first material comprising an organic material and a second material comprising an inorganic material.

13. The method of claim 1, wherein forming the layer of the article of manufacture comprises depositing a first material comprising a biological material.

14. The method of claim 13, wherein depositing the first material comprising the biological material comprises depositing living cells.

15. The method of claim 14, wherein depositing the at least two materials comprises depositing a second material comprising a nutrient for the living cells.

16. The method of claim 15, wherein depositing the at least two materials comprises depositing a third material comprising a carrier for the living cells.

17. The method of claim 1, wherein forming the layer of the article of manufacture comprises depositing a first material comprising a pharmaceutical material.

18. The method of claim 17, wherein forming the layer of the article of manufacture comprises depositing a second material comprising an excipient.

19. A method for fabricating an article of manufacture, comprising:
   forming a layer of the article of manufacture based on a digital model of the article of manufacture using an additive manufacturing system, the layer formed from at least two materials in liquid form that differ from one another, the at least two materials being miscible, at least one of the at least two materials able to dissolve at least another material of the at least two materials, and or the at least two materials able to react with one another; and
   repeating the forming at least once to form another layer of the article of manufacture, the another layer of the article of manufacture being at least partially superimposed with the layer of the article of manufacture, the at least two materials forming a blended zone including portions of the layer and the another layer, portions of adjacent areas of the layer, and/or portions of adjacent areas of the another layer.

* * * * *